United States Patent

Hermansson et al.

Patent Number: 5,306,673
Date of Patent: Apr. 26, 1994

[54] COMPOSITE CERAMIC MATERIAL AND METHOD TO MANUFACTURE THE MATERIAL

[75] Inventors: Leif Hermansson, Uppsala; Sevald Forberg, Enskede; Li Jiangou, Stockholm, all of Sweden

[73] Assignee: Stiftelsen Centrum for Dentalteknik och Biomaterial i Huddinge, Huddinge, Sweden

[21] Appl. No.: 752,605
[22] PCT Filed: Mar. 30, 1990
[86] PCT No.: PCT/SE90/00207
  § 371 Date: Aug. 15, 1991
  § 102(e) Date: Aug. 15, 1991

[30] Foreign Application Priority Data

Apr. 10, 1989 [SE] Sweden ............. 8901294-2

[51] Int. Cl.⁵ .......... C04B 35/10; C04B 35/46; C04B 35/48
[52] U.S. Cl. ............ 501/1; 501/123; 501/125; 264/65; 264/570; 264/60
[58] Field of Search .......... 264/65, 570, 60; 501/123, 125, 1

[56] References Cited

U.S. PATENT DOCUMENTS

| | | | |
|---|---|---|---|
| 4,149,893 | 4/1979 | Aoki et al. | 501/123 |
| 4,599,085 | 7/1986 | Reiss | 75/230 |
| 4,957,674 | 9/1990 | Ichitsuka | 264/65 |

FOREIGN PATENT DOCUMENTS

| | | |
|---|---|---|
| 2928007 | 1/1981 | Fed. Rep. of Germany . |
| 3301122 | 7/1984 | Fed. Rep. of Germany . |
| 62-142565 | 6/1987 | Japan . |
| 62-197066 | 8/1987 | Japan . |

OTHER PUBLICATIONS

Chemical Abstracts vol. 108, No. 2, Abstract 11277u Jan., 1988.
Hot Isostatic Press, Kobe Steel, No. 428090, pp. 1-6, Aug., 1982.

*Primary Examiner*—James Derrington
*Attorney, Agent, or Firm*—Griffin, Butler, Whisenhunt & Kurtossy

[57] ABSTRACT

The present invention relates to a method to manufacture a composite ceramic material having a high strength combined with bioactive properties, when the material is used as a dental or orthopedic implant, which includes preparing a powder mixture, mainly comprising partly a first powder, which in its used chemical state will constitute a bioinert matrix in the finished material, and partly a second powder, mainly comprising a calcium phosphate-based material. The invention is characterized in that said first powder comprises at least one of the oxides belonging to the group consisting of titanium dioxide ($TiO_2$), zirconium oxide ($ZrO_2$) and aluminum oxide ($Al_2O_3$), in that said second powder mainly comprises at least one of the compounds hydroxylapatite and tricalcium phosphate, in that a raw compact is made of said powder mixture and in that said raw compact is densified through an isostatic pressing in a hot condition (HIP) at a pressure higher than 50 MPa, a composite material being obtained, in which said matrix comprises one or several metal oxides of said first powder, in which matrix said compound hydroxylapatite and/or tricalcium phosphate is evenly dispersed.

The invention also relates to a composite ceramic material as well as a body, completely or partially made of this material.

12 Claims, 2 Drawing Sheets

COMPOSITE CERAMIC MATERIAL AND METHOD TO MANUFACTURE THE MATERIAL

TECHNICAL FIELD

The present invention relates to a composite ceramic material having a high strength combined with bioactive properties when the material is used as a dental or orthopedic implant. The invention relates also to a method to manufacture the composite ceramic material.

BACKGROUND ART

Ceramic materials and particularly structural ceramic materials generally have a high resistance to corrosion and erosion. This is true of e.g. several oxides, nitrides, carbides and borides. Also, said materials have no toxic properties. When used as implant materials said materials are completely inactive, i.e. neither positive nor negative reactions with surrounding tissues take place, and consequently it is possible to attain a biological integration to bone tissue without any intermediate connective tissue. Such materials are termed inert when used as implant materials. These properties make several oxides, nitrides, carbides and borides potentially very valuable as inert dental and orthopedic implant materials.

However, it is desirable that materials having a favorable biocompatibility are not only inert, i.e. able to fasten mechanically to a bone tissue, but also bioactive, i.e. the implant can be bonded chemically to a bone tissue. Oxides, nitrides, carbides and borides do not have this property. On the other hand it is known that phosphate-based materials, having a chemical composition similar to the "inorganic" or "ceramic" matter in bone tissue, can display bioactive properties. Such a phosphate-based material is e.g. hydroxylapatite, $Ca(PO_4)_3$. However, a synthetic hydroxylapatite has a low tensile toughness and hence a low strength and also a tendency to gradually develop a continuous crack growth. Another example of a bioactive material having a calcium phosphate-base is tricalcium phosphate $Ca_3(PO_4)_2$, but this compound has an unsatisfactory strength. Also, it has a not negligible water solubility and consequently may be dissolved before the bond to the bone tissue has developed. Thus, in this respect, hydroxylapatite is preferred as compared to tricalcium phosphate.

DISCLOSURE OF THE INVENTION

The object of the invention is to suggest a composite ceramic material having a so called duo-quality, i.e. a high strength combined with a bioactivity. This and other objects can be attained by using a material, which comprises, when it is used as an implant material, an inert matrix having a high strength and in the matrix evenly distributed 5 -35 percent by volume of at least one second phase, which mainly comprises at least one material having a calcium phosphate-base. This calcium phosphate-base can e.g. be hydroxylapatite and/or tricalcium phosphate, while the matrix can comprise mainly one or several oxides and/or nitrides. The matrix comprises preferably mainly one or several oxides belonging to the group which comprises titanium dioxide, zirconium oxide and aluminum oxide.

The used hydroxylapatite can be entirely synthetic or consist of a bone ash, which also contains other compounds than hydroxylapatite in small contents.

The material is produced by preparing a powder mixture, which mainly consists of partly a first powder, which in the condition the powder material is in during the admixture or it will obtain after a subsequent chemical reaction can form a biologically inert matrix in the finished material when it is to be used as an implant material, and partly a second powder, mainly consisting of a material having a calcium phosphate-base. A raw compact is made of this powder mixture and densified by a hot isostatic pressing at a temperature of 900°–1300° C. and a pressure higher than 50 MPa, preferably at a pressure of at least 150 MPa and preferably not more than 250 MPa. The raw compact (green body) is in this case suitably produced by a cold isostatic compacting, which precedes the hot isostatic compacting, which is facilitated by the admixture of the calcium phosphate powder into the oxide powder. Despite the comparatively low temperature during the hot isostatic compacting it is possible to attain a density of at least 97%, if the matrix consists of oxides. The comparatively low sintering temperature is advantageous, e.g. for the following reasons:

The grain growth is limited, which favors a high strength;

A decomposition of the calcium phosphate material (hydroxylapatite or the like) is avoided or limited to an acceptable extent; and Undesirable reactions between oxides, e.g. titanium dioxide, and the calcium phosphates are prevented.

When the powder material is consolidated, no chemical reactions take place. The powder mixture suitably is composed in such a manner, that the calcium phosphate-phase will appear as small islands, i.e. as discrete particles, in the matrix, which according to the first preferred embodiment of the invention consists of one or several oxides belonging to the group, which comprises titanium dioxide, zirconium oxide and aluminum oxide. One might expect that 5 -35 percent by volume of calcium phosphate material in the inert matrix is not sufficient to ensure the desired bioactivity but at the same time will result in a risk of a substantial deterioration of the strength properties. However, we have found that these fears are groundless. Thus, clinical experiments, performed on living animals, have shown, that the material according to the invention has a bioactivity, which is entirely comparable to the bioactivity of pure hydroxylapatite. Thus, it is not necessary to coat the inert matrix with pure hydroxylapatite in order to obtain the desirable bioactivity, which otherwise is customary according to known practice. However, the admixture of calcium phosphate material into the matrix probably must be very finely dispersed and even in order to obtain a very large number of islands per exposed surface unit, the distance between, adjacent islands of calcium phosphate at the same time being very small. These conditions probably will facilitate the addition of a new bone tissue, but the causal relations have not been completely explained. The very finely dispersed and even nature of the distribution of the calcium phosphate fraction in the matrix can also explain the retained very high strength. Thus, provided one regards the calcium phosphate particles as defects of the matrix, it is possible to calculate the largest possible size of the calcium phosphate islands in different oxide materials in order to obtain a certain so called critical intensity factor (critical toughness), known for the matrix. Thus, if the matrix is tougher, the islands can be larger than in a brittle matrix and vice versa. These theoretical considerations and practical results lead to the following recommendations for a composite consolidated material consisting of a matrix, which comprises metal oxides, and a calcium phosphate material dispersed in the matrix, preferably hydroxylapatite.

| Matrix | Maximum size of the calcium phosphate particles | Mean distance between the calcium phosphate particles | |
|---|---|---|---|
| $TiO_2$ | 10 μm | Max. 5 μm, pref. | max. 2 μm |
| $Al_2O_3$ | 15 μm | " | " |
| $ZrO_2$ | 30 μm | " | " |

Thus, as regards the strength, zirconium oxide is preferred to aluminum oxide, which in its turn is better than titanium oxide. Also, the oxides differ as to their chemical resistance. Thus, whereas the temperature during the hot isostatic pressing should not be higher than 1000 °C., when the matrix is composed of titanium dioxide, it can be as high as 1300 °C. and preferably 1100-1250° C., when a matrix of aluminum oxide and/or zirconium oxide is used.

Whereas according to known practice one believes that it is necessary to provide an implant with a coat, which entirely consists of a bioactive material, which means that in certain cases the implant has been provided with an outer coat of a calcium phosphate material, according to the present invention it is possible to use the duo-properties of the composite material according to the invention, alone and an extra outer coat of hydroxylapatite or the like is not being necessary. However, it is also, within the scope of the present invention, possible per se to cover a "duo-material", completely or partially, with layers of materials having another composition or to produce implants, in which different parts have different compositions, including at least one part consisting of a composite material according to the invention having duo-properties and at least one part consisting of a homogenous material, e.g. a ceramic material without any admixture of a calcium phosphate material or an entirely metallic material. These and other aspects of the invention are also set forth in the patent claims and will be further elucidated in the following description of a few preferred embodiments.

BRIEF DESCRIPTION OF DRAWINGS

The invention will now be explained in more detail by means of a few illustrative examples and experiments carried out, reference being made to the accompanying drawings, in which.

DESCRIPTION OF EXPERIMENTS CARRIED OUT AND EMBODIMENTS

Figure 1:
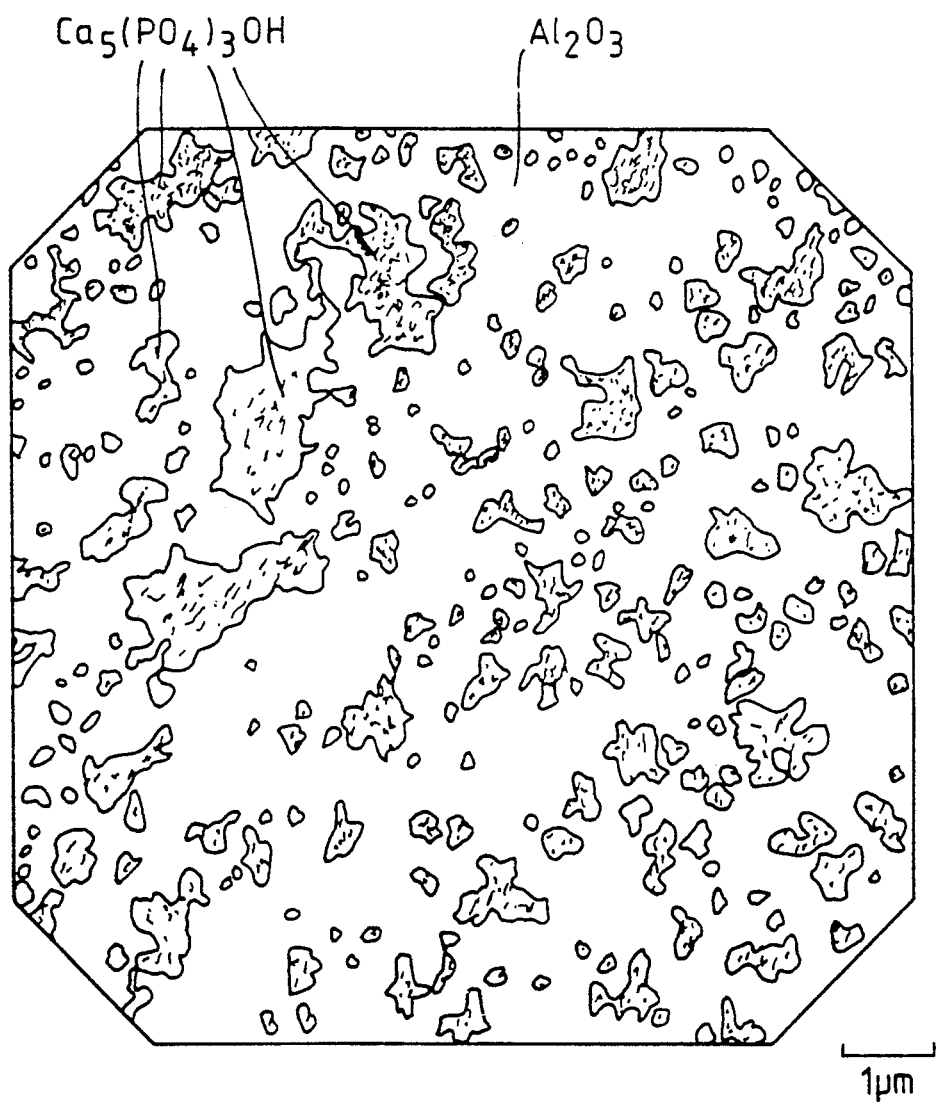
FIG. 1 shows a microstructure of a material according to a first preferred embodiment according to the invention.

Raw materials used in the trials are listed in Table 1. Monolithic materials (titanium dioxide and hydroxylapatite respectively) as well as composite materials (combinations of oxides and calcium phosphate materials), see Table 2, were produced from powders of these raw materials. The powder mixtures and a silicon nitride grinding agent in petroleum ether were admixed in a ball mill and were ground for 20 h. Subsequent to an evaporation in an evaporator raw compacts were produced from the powder mixtures by a cold isostatic compacting (CIP) at a pressure of 300 MPa. The raw compacts thus obtained were encased in glass and densified by a hot isostatic pressing (HIP) at a pressure of 200 MPa for 1 h at a maximum temperature of 925° C. for the $TiO_2$- based materials and at 1225° C. for the other materials. Subsequent to the densification the materials displayed a density of more than 99% of the theoretical maximum density. The HIP-temperatures and the obtained densities are also shown in Table 2.

TABLE 1

| Raw materials | |
|---|---|
| Designation | Description |
| BA | Hydroxylapatite of bone ash |
| HA | Hydroxylapatite, grade Merck |
| TCP | β-tricalcium phosphate, grade Merch |
| A | α-aluminum oxide, AKP-30, Sumitomo |
| R | Titanium dioxide, Tioxide Ltd |
| Z | Zirconium dioxide (including 3 mol % $Y_2O_3$) |

TABLE 2

Powder mictures which have been compacted by a hot isostatic pressing; densities of HIP-produced specimens

| Specimen No. | Powder, % by volume | HIP-temp. °C. | Density g/cm³ Recorded | Theoretical |
|---|---|---|---|---|
| 1 | 70HA/30A | 1225 | 3.39 | 3.40 |
| 2 | 25HZ/75A | 1225 | 3.75 | 3.77 |
| 3 | 15BA/85A | 1225 | 3.85 | 3.85 |
| 4 | 15HA/85R | 925 | 4.02 | 4.09 |
| 5 | 7.5TCP/7.5HA/85A | 1225 | 3.77 | 3.85 |
| 6 | 7.5TCP/7.5HA/85R | 925 | 4.04 | 4.09 |
| 7 | 15HA/85Z | 1225 | 5.64 | 5.65 |

TABLE 3

| Specimen no. | Tensile strength (MPa) | Weibull-module (m) | Toughness (MPam$^{\frac{1}{2}}$) | Hardness (5N) (GPa) |
|---|---|---|---|---|
| HA | 110 | 18 | 1.1 ± 0.1 | 3.9 ± 0.3 |
| 1 | 250 | n.d.* | 2.0 | 7.1 |
| 2 | 535 | n.d.* | 4.0 | 20.2 |
| 3 | 601 | 19 | 3.5 | 18.9 |
| 4 | 252 | 9 | 2.9 | 8.4 |
| 5 | 446 | 10 | 3.4 | 17.8 |
| 6 | 397 | n.d.* | 2.6 | 10.9 |
| 7 | 820 | n.d.* | >7 | 13 |
| A | 400-560 | — | 4 | 22 |
| R | 405 | 10 | — | 12 |
| Z | 980 | n.d.* | >7 | 14 |

*not measured

Test bars were made with the size 3×3×30 mm. The test bars were examined in a three-point test to measure the compressive strength in bending. The Weibull-modules were measured. The toughness was measured using Vicker's indentation depth method, as well as the hardness at a load of 10N och 5N respectively. Some specimens were etched for 20 seconds in a 0.1% HF-solution in order to study the microstructure in SEM.

In order to study the bioactive properties of the materials cylinders were made with a diameter of 3.1 mm and a length of 7 mm. Identical specimens of pure aluminum oxide (negative control) and pure hydroxylapatite (positive control) were also made to be used as reference materials. The implants were inserted by operation in a large hole (3.2 mm diameter) in lateral cortex in rabbits (femora-rabbit fran New Zeeland). After a healing period of three months the animals were put to death and the implants were examined by X-ray radiography, subsequent to the removal of surrounding soft tissue.

FIG. 1 shows the microstructure of a material according to the invention, being composed of 15 percent by volume hydroxylapatite, the remainder being aluminum oxide (specimen 3). The hydroxylapatite-phase is evenly distributed throughout the aluminum oxide-matrix, in which the hydroxylapatite forms particles (grains) or islands (insulets) having a maximum length of <6 $\mu$m . The specimen is somewhat overetched in FIG. 1 in order to be able to identify the microstructure more easily. Some of the smallest grains can be pores. An X-ray diffraction analysis showed that no phase alterations had taken place during the HIP-treatment.

The mechanical properties are shown in Table 3. As is expected, the aluminum oxide-based duo-ceramic materials, specimens 1, 2, 3 and 5, are stronger than the titanium dioxide based materials, specimens 4 and 6. The strength level of the aluminum oxide-based duo-ceramic materials is comparable to the strength level of commercial dental implants made of polycrystalline aluminum oxide, which is 400-560 MPa. The tensile strength is also comparable. The zirconium oxide-based duo-ceramic materials have the highest strength and tensile strength. The results show, that the duo-ceramic materials according to the present invention can be used for dental implants, at least as regards the mechanical properties. This is particularly true of those duo-ceramic materials according to the invention, which are based on aluminum oxide and zirconium oxide, but also the titanium-based duo-ceramic materials in all likelihood can be used as implants, at least in those instances when the mechanical properties are a critical factor.

Figure 2:
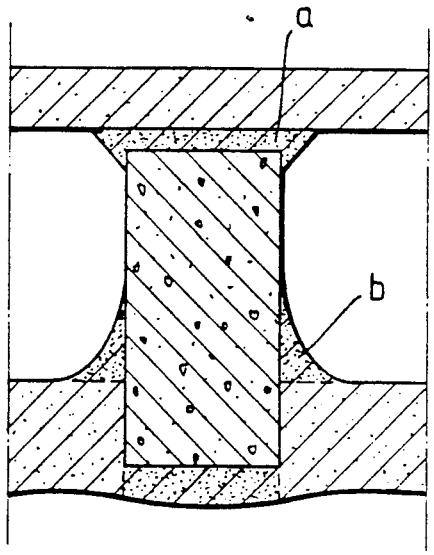
FIG. 2 is a drawn picture, based on an X-ray photograph, which shows how an implant according to the invention has adhered to a natural bone material.

FIG. 2 shows in a drawing, based on an X-ray radiograph a ceramic cylinder, made of specimen no. 3 in Table 3 and inserted by operation. A new cortical bone material has grown towards the implant (at a) as well as along the surface of the implant (at b). The pattern of bone growth for the duo-ceramic material according to the invention is mainly identical with that for pure hydroxylapatite, as was shown in a comparison test. A similar pattern was also obtained with specimens no.4 and no. 7, which had a matrix of titanium dioxide and zirconium oxide respectively.

These trials show, that bioactive ceramic materials having a high strength can be produced by means of a hot isostatic pressing of a raw compact, which is composed of at least two powder fractions, a bioactive phase being obtained, which consists of hydroxylapatite and is evenly distributed in an oxidic matrix, which gives the material the required strength. The bioactive phase appears as distinct points, the size of which can be allowed to vary depending on the strength of the matrix, but the mean distance between adjacent points must be smaller than 5 $\mu$m, preferably smaller than 2 $\mu$m.

In the description above for the invention it has been mentioned that it, within the scope of the inventive concept, also is possible to produce compacts (bodies), in which different parts have different compositions. This will now be illustrated by means of a few possible examples. According to a first embodiment of this aspect of the invention 15 percent by volume hydroxylapatite powder and 85 percent by volume zirconium oxide powder are mixed. The powder is prepared in the same manner as is explained in the description above of experiments carried out. The powder mixture is poured into a polymer can to fill the can up to half its height. Pure aluminum oxide without any admixture of any substance is then added to fill the can completely. The can is closed and the powder is isostaticly compressed in a cold condition at 300 MPa. The compact specimen is then isostaticly compressed in a hot condition at 1225° for 1 h and at a pressure of 160 MPa. The compact specimen is cut into test bars, in which the center line roughly corresponds to the boundary between pure aluminum oxide and the aluminum oxide/hydroxylapatite-mixture. The test bars (7 of them) with the dimensions 35×3×3 mm are examined using a three-point-bend-testing method. A mean value of the tensile strength was measured to 720 MPa (the lowest value was 540 MPa and the highest 810 MPa).

Figure 3:
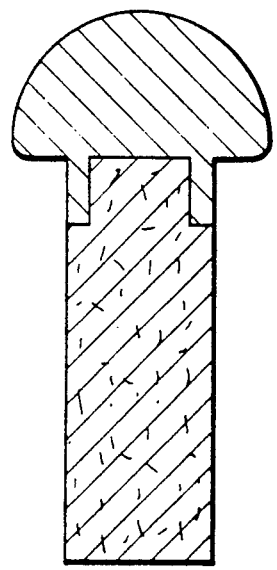
FIG. 3 shows a longitudinal section of a product according to a possible embodiment of the invention.

It is also possible to produce a material similar to the previous one by producing two separate raw compacts, one of them consisting of a powder mixture of a calcium phosphate powder and an oxidic powder and the other one solely consisting of an oxidic powder, and combining the raw compacts through a common isostatic compacting in a hot condition. FIG. 3 shows schematicly an example of a work piece produced in this way, in which the joint-ball can consist of a ceramic substance made of pure oxide and the stem can consist of a duo-ceramic substance according to the invention.

Figure 4:
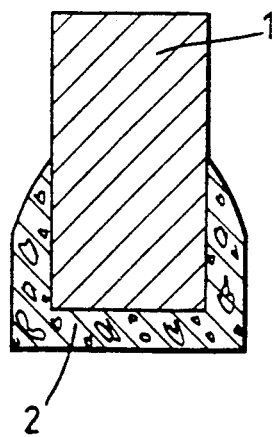
FIG. 4 shows a longitudinal section of a product according to another possible embodiment of the invention.

FIG. 4 shows schematicly another example. In this instance a pure oxidic powder 1 is coated with a duo-ceramic powder 2, powder 2 being partially covering powder 1, subsequent to which the combined powder is isostaticly compressed in a cold condition and after that is encased and isostaticly compressed in a hot condition.

Figure 5:
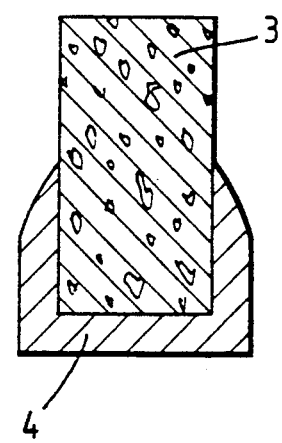
FIG. 5 shows a longitudinal section of a product according to an additional possible embodiment of the invention.

FIG. 5 shows the opposite instance, namely that a raw compact 3 of a duo-ceramic powder according to the invention partially is coated with an oxidic powder 4, before the compact is consolidated through a combined isostatic pressing in a cold condition followed by an isostatic pressing in a hot condition.

A compact of a duo-ceramic material according to the invention can also be treated in order to remove the bioactive phase in the surface area of a section of the component. This can be done through a chemical dissolving of the calcium phosphate phase in the surface layer or through blasting. In either case small cavities are obtained in those areas where the phosphate material previously was present and these cavities can function as liquid reservoirs, in case implants for joints are to be produced. Thus, a certain amount of liquid can be kept and in this way the friction can be reduced within those areas, where a sliding is to take place in the joint. Of course, the remaining parts of the duo-ceramic work-piece are to be left intact in order to be able to utilize the bioactive properties of the duo-ceramic work-piece, where this property is desirable.

We claim:

1. A method for producing a ceramic material having high strength and bioactive properties and useful as dental and orthopedic implants, comprising:
   (1) forming a mixture of matrix powder containing a bioinert material selected from the group consisting of titanium dioxide, zirconium oxide, aluminum oxide and mixtures thereof and a bioactive powder containing a bioactive material selected from the group consisting of hydroxylapatite, tricalcuim phosphate and mixtures thereof, wherein 5 to 35% by volume of the bioactive material is contained in the mixture;
   (2) forming a raw compact of the mixture;
   (3) subjecting the raw compact to hot isostatic pressing at pressures greater than 50 MPa and at temperatures between 900° C. and 1300° C. sufficiently to density the raw compact to at least 97% of theoretical maximum density and to substantially uniformly disperse the bioactive material in the bioinert material such that the bioactive material is in particle form with particle sizes thereof of up to 30 μm and the maximum mean distance between particles is about 5 μm.

2. Method according to claim 1 wherein the raw compact is densified at a pressure of at least 150 MPa and not more than 250 MPa.

3. Method according to claim 2, wherein the bioinert material is titanium dioxide and the raw compact is densified at a temperature of 900-1000 ° C.

4. Method according to claim 2, wherein the bioinert material is aluminum oxide and/or xirconium oxide and the raw compact is densified at a temperature of 1100°-1250° C.

5. Method according to claim 1, wherein the bioactive material is hydroxylapatite $Ca_5(PO_4)_3OH$.

6. Method according to claim 1, wherein the mixture has 10-25 percent by volume of said bioactive material therein.

7. A ceramic material having high strength and bioactive properties and useful as dental and orthopedic implants, comprising a high temperature, isostatically formed shape of a matrix material containing a bioinert material selected from the group consisting of titanium dioxide, zirconium oxide, aluminum oxide and mixtures thereof and dispersed material containing a bioactive material selecteg from the group consisting of hydroxylapatite, tricalcium phosphate and mixtures thereof, wherein the bioactive material is substantially uniformly dispersed in the matrix material in amounts between about 5 and 35% by volume and in particle form having particle sizes of up to 30μm with maximum mean distances between particles of about 5 μm and wherein the density of the high temperature isostatically formed shape is at least 97% of theoretical maximum density, and wherein the formed shape is hot isostatically pressed at temperatures between 900 °C. and 1300° C. and at a pressure higher than 50 MPa.

8. Material according to claim 7, wherein the bioinert material is zirconium oxide.

9. Material according to claim 7, wherein the bioinert material is aluminum oxide and the maximum particle size of the bioactive material is 15 μm.

10. Material according to claim 7, wherein the bioinert material is titanium dioxide and the maximum particle size of the bioactive material is 10 μm.

11. A body partially made of a material according to claim 7, wherein one or several parts of said body are made of the bioinert material.

12. The material of claim 7 wherein the maximum distance between particles is about 2 μm.

* * * * *